United States Patent
Jing et al.

(10) Patent No.: US 12,357,637 B2
(45) Date of Patent: Jul. 15, 2025

(54) SOLID PHARMACEUTICAL COMPOSITION COMPRISING TLR7 AGONIST

(71) Applicant: Chia Tai Tianqing Pharmaceutical Group Co., Ltd., Lianyungang (CN)

(72) Inventors: Jianghui Jing, Lianyungang (CN); Lihui Dong, Lianyungang (CN); Yi Xu, Lianyungang (CN); Xinlu Li, Lianyungang (CN); Xifeng Lu, Lianyungang (CN); Shang Wang, Lianyungang (CN); Haishan Zang, Lianyungang (CN); Min Li, Lianyungang (CN); Zhilin Chen, Lianyungang (CN); Xiandong Zhao, Lianyungang (CN); Peng Sun, Lianyungang (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 835 days.

(21) Appl. No.: 17/594,439

(22) PCT Filed: Apr. 23, 2020

(86) PCT No.: PCT/CN2020/086301
§ 371 (c)(1),
(2) Date: Oct. 15, 2021

(87) PCT Pub. No.: WO2020/216274
PCT Pub. Date: Oct. 29, 2020

(65) Prior Publication Data
US 2022/0184085 A1    Jun. 16, 2022

(30) Foreign Application Priority Data
Apr. 23, 2019   (CN) .......................... 201910326899.9

(51) Int. Cl.
*A61K 31/519*      (2006.01)
*A61K 9/20*         (2006.01)

(52) U.S. Cl.
CPC .......... *A61K 31/519* (2013.01); *A61K 9/2009* (2013.01); *A61K 9/2013* (2013.01); *A61K 9/2054* (2013.01); *A61K 9/2059* (2013.01); *A61K 9/2095* (2013.01)

(58) Field of Classification Search
CPC ... C07D 487/04; A61K 31/519; A61K 9/2009
See application file for complete search history.

(56) References Cited

U.S. PATENT DOCUMENTS 9,962,388 B2 *   5/2018   Ding ................... C07D 487/04

FOREIGN PATENT DOCUMENTS

| CN | 107550875 A | 1/2018 |
| TW | I558709 B | 11/2016 |
| WO | WO 2016/023511 A1 | 2/2016 |
| WO | WO 2017/133684 A1 | 8/2017 |
| WO | WO 2020/188448 A1 | 9/2020 |

OTHER PUBLICATIONS

Smekhova, I.E. et al., "Disintegrants and their Influence on the Dissolution of Substances of Biopharmaceutical Classification System Classes" 2018, pp. 62-72, vol. 4, No. 25.
Office Action for RU 2021132040 issued Dec. 27, 2023.
Supplementary European Search Report for EP 20795435 issued Dec. 16, 2022.
Meeus, Liesbeth. "Direct compression versus granulation." *Pharmaceutical Technology Europe* 23.3 (2011): pp. 21-22.
Rowe, Raymond C., et al.(eds.) *Handbook of Pharmaceutical Excipients*. Pharmaceutical Press, Fifth Edition, Pharmaceutical Press, Chicago, 2006.
Office Action in Taiwan Patent Application No. 109113649, dated Aug. 2, 2023.
Office Action in Russian Patent Application No. 2021132040, dated Sep. 6, 2023.
Handbook of Pharmaceutical Excipients (6th edition), Raymond C. Rowe et al., 2009, pp. 129-130.
Huang, Zhaoxia "Progress in Direct Powder Tableting Process" Journal of Modern Food and Pharmaceuticals, Oct. 2007, pp. 31-36, vol. 17, No. 5.
International Search Report for PCT/CN2020/086301 dated Jun. 5, 2020.

\* cited by examiner

*Primary Examiner* — Kamal A Saeed
(74) *Attorney, Agent, or Firm* — Knobbe, Martens, Olson & Bear, LLP

(57) ABSTRACT

A solid pharmaceutical composition comprising a TLR7 agonist 2-butoxy-7-(4-(pyrrolidin-1-ylmethyl)benzyl)-5H-pyrrolo[3,2-d]pyrimidin-4-amine, a preparation method therefor, and an medical application thereof. The solid pharmaceutical composition has excellent stability and dissolution properties.

15 Claims, No Drawings

SOLID PHARMACEUTICAL COMPOSITION COMPRISING TLR7 AGONIST

CROSS-REFERENCES TO RELATED APPLICATIONS

This application is a U.S. National Phase Application of PCT International Application Number PCT/CN2020/086301, filed on Apr. 23, 2020, designating the United States of America and published in the Chinese language, which is an International Application of and claims the benefit of priority to Chinese Patent Application No. 201910326899.9, filed on Apr. 23, 2019. The disclosures of the above-referenced applications are hereby expressly incorporated by reference in their entireties.

TECHNICAL FIELD

The present application belongs to the field of pharmaceutical chemistry, and particularly relates to a solid pharmaceutical composition comprising a TLR7 agonist (2-butoxy-7-(4-(pyrrolidin-1-ylmethyl)benzyl)-5H-pyrrolo[3,2-d]pyrimidin-4-amine), a preparation method therefor, and medical use thereof.

BACKGROUND

Toll-like receptors are expressed in a variety of immune cells. Toll-like receptors recognize highly-conserved structural motifs: pathogen-associated molecular patterns (PAMPs) expressed by microbial pathogens or damage-associated molecular patterns (DAMPs) released by necrotic cells. Toll-like receptors are stimulated by corresponding PAMPs or DAMPs to induce signaling cascade, leading to activation of transcription factors such as AP-1, NF-κB and an interferon regulation factor (an impulse response function). As such, a variety of cellular reactions are induced, including production of interferons, pro-inflammatory cytokines and effector cytokines, thus promoting immune response. So far, 13 Toll-like receptors have been found in mammals. Toll-like receptors 1, 2, 4, 5 and 6 are mainly expressed on cell surfaces while toll-like receptors 3, 7, 8 and 9 are expressed in endosomes. Different toll-like receptors can recognize ligands derived from different pathogens. Toll-like receptor 7 (TLR7) is mainly expressed in plasmacytoid dendritic cells (pDCs), and induces secretion of the interferon alpha (IFN-α) by ligand recognition. Toll-like receptor 7 (TLR7) and toll-like receptor 8 (TLR8) are highly homologous, and thus TLR7 ligands are further TLR8 ligands in many cases. TLR8 is stimulated to mainly induce the production of cytokines, such as tumor necrosis factor alpha (TNF-α) and chemokines. Interferon alpha is one of the main drugs for use in treating chronic hepatitis B or hepatitis C, while TNF-α is a pro-inflammatory cytokine, and its excessive secretion may cause serious side effects.

WO2016/023511 discloses certain compounds used as a TLR7 agonist. There remains a need in the art to develop a suitable pharmaceutical composition comprising a TLR7 agonist compound.

SUMMARY

In one aspect, the present application relates to a solid pharmaceutical composition, which comprises a compound of formula I, a diluent, a binder, a disintegrant, and a lubricant,

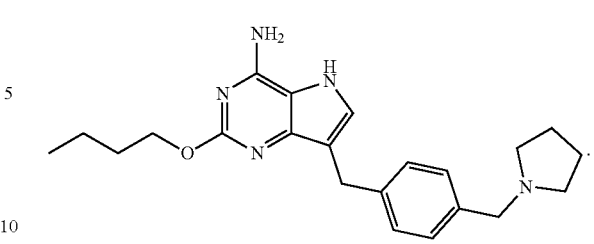

In one embodiment, the diluent is selected from the group consisting of microcrystalline cellulose, mannitol, lactose, sucrose, starch, pregelatinized starch, dextrin, and a mixture thereof; preferably, microcrystalline cellulose, mannitol, lactose, pregelatinized starch, and a mixture thereof; more preferably, microcrystalline cellulose, pregelatinized starch, and a mixture thereof.

In one embodiment, the binder is selected from the group consisting of hydroxypropyl methylcellulose, carboxymethylcellulose, carboxymethylcellulose sodium, ethylcellulose, methylcellulose, hydroxypropylcellulose, low-substituted hydroxypropylcellulose, gelatin, polyvinylpyrrolidone, partially hydrolyzed starch, pregelatinized starch, glucose, polyethylene glycol, polyvinyl alcohol, and a mixture thereof; preferably, hydroxypropyl methylcellulose, carboxymethylcellulose, carboxymethylcellulose sodium, ethylcellulose, methylcellulose, hydroxypropylcellulose, low-substituted hydroxypropylcellulose (L-HPC), polyvinylpyrrolidone, and a mixture thereof; more preferably, hydroxypropyl methylcellulose. In one embodiment, the disintegrant is selected from the group consisting of sodium carboxymethyl starch, dry starch, microcrystalline cellulose, hydroxyethyl methylcellulose, carboxymethylcellulose sodium, carboxymethylcellulose calcium, croscarmellose sodium, low-substituted hydroxypropyl methylcellulose or crospovidone, sodium dodecyl sulfate or magnesium dodecyl sulfate, and a mixture thereof; preferably, sodium carboxymethyl starch, croscarmellose sodium, and a mixture thereof; more preferably, sodium carboxymethyl starch. In one embodiment, the lubricant is selected from the group consisting of magnesium stearate, colloidal silicon dioxide (colloidal silica), talc, polyethylene glycol 4000, polyethylene glycol 6000, stearic acid, sodium stearyl fumarate, sodium dodecyl sulfate, and a mixture thereof; preferably, magnesium stearate, colloidal silicon dioxide, sodium dodecyl sulfate, and a mixture thereof; more preferably, magnesium stearate, colloidal silicon dioxide, and a mixture thereof.

In another aspect, the present application further relates to a method for preparing the solid pharmaceutical composition disclosed herein, which comprises a direct compression method.

In yet another aspect, the present application further relates to use of the solid pharmaceutical composition disclosed herein for the manufacture of a medicament for the treatment or prevention of a disease associated with TLR7. In one embodiment, the disease associated with TLR7 is selected from a viral infectious disease. In a preferred embodiment, the viral infectious disease is selected from the group consisting of hepatitis B and hepatitis C.

DETAILED DESCRIPTION

Definitions and Description

Unless otherwise indicated, the terms and phrases used herein have the meanings set forth below. A specific term or phrase, unless otherwise specifically defined, should not be considered uncertain or unclear, but construed according to its common meaning understood by those skilled in the art. When referring to a trade name, it is intended to refer to its corresponding commercial product or its active ingredient.

Unless specifically defined otherwise or different from the usual usage, proportions (including percentages) or parts used herein are calculated by weight, e.g., % wt or wt %.

The term "comprise", "comprises" or "comprising" or similar words synonymous therewith "include", "includes" or "including", "contain", "contains" or "containing" and "have", "has" or "having" and the like are open-ended and do not exclude additional unlisted elements, steps or components. The phrase "consisting of" excludes any element, step or component that is not specified. The phrase "consisting essentially of" refers to that the scope is limited to the specified elements, steps or components, plus elements, steps or components that are optionally present and do not materially affect the basic and novel characteristics of the claimed subject matter. It should be understood that the term "comprise", "comprises" or "comprising" encompasses the phrases "consisting essentially of" and "consisting of".

The term "optional" or "optionally" refers to that the subsequently described event or circumstance may occur or may not occur. The description includes instances where the event or circumstance occurs and instances where the event or circumstance does not occur.

In the present application, "one or more" or "at least one" may represent 1, 2, 3, 4, 5, 6, 7, 8, 9 or more. Accordingly, "two or more" may represent 2, 3, 4, 5, 6, 7, 8, 9 or more.

In the present application, the compound of formula I includes the compound in a free base form and in a pharmaceutically acceptable salt form. The "pharmaceutically acceptable salt" includes, but is not limited to, trifluoroacetate salt or maleate salt.

In the present application, the content of the compound of formula I in the pharmaceutical composition is calculated in the free base form.

The amount "% wt" of a certain ingredient (including an active substance or excipient) described herein refers to a weight percentage of the ingredient in the total weight of the solid pharmaceutical composition (wherein the weight of the compound of formula I is calculated in the free base form). The total weight of the solid pharmaceutical composition does not include the weight of the coating agent.

The preparation method for the solid pharmaceutical composition described herein may be carried out according to methods well known in the art. The specific preparation method may comprise steps of pulverizing, mixing, sieving, granulating, filling, tableting, etc. The required steps and the method or equipment for implementing the specific steps are selected according to actual conditions. For example, the pulverizing step may be performed by using a mortar, a ball mill, a roller press, an impact mill, a hammer mill and/or a jet mill; the mixing step may be agitation mixing, grinding mixing and/or sieving mixing; the sieving step may be performed by using a sieve shaker and/or a vibrating screen. Or referring to *Pharmacy* (6th or 7th Edition, People's Medical Publishing House) edited by Cui Fude et al.

As used herein, the "preparing into a mixture" may be accomplished by one or more steps in the preparation process of the solid pharmaceutical composition. Illustratively, for example, "preparing the compound of formula I, the diluent, the disintegrant, the binder and the lubricant into a mixture" may be accomplished by mixing all of the components in one step; or, a multi-step mixing method may be used, in which some of the components are mixed first and then the rest of the components are mixed.

The term "treat", "treating" or "treatment" refers to administering the compound or the pharmaceutical composition described herein so as to ameliorate or eliminate a disease or one or more symptoms associated with the disease, and includes: (i) inhibiting the disease or disease state, i.e., arresting its development; and (ii) alleviating the disease or disease state, i.e., causing regression of the disease or disease state.

The term "prevent", "preventing" or "prevention" refers to administering the compound or the pharmaceutical composition described herein so as to prevent a disease or one or more symptoms associated with the disease, and includes: preventing the occurrence of the disease or disease state in a mammal, particularly when such a mammal is predisposed to the disease state but has not yet been diagnosed as having it.

The term "therapeutically effective amount" refers to an amount of the compound disclosed herein for (i) treating or preventing a specific disease, condition or disorder; (ii) alleviating, ameliorating or eliminating one or more symptoms of a specific disease, condition or disorder, or (iii) preventing or delaying onset of one or more symptoms of a specific disease, condition or disorder described herein. The amount of the compound disclosed herein composing the "therapeutically effective amount" varies dependently on the compound, the disease state and its severity, the mode of administration, and the age of the mammal to be treated, but can be determined routinely by those skilled in the art in accordance with their knowledge and the present disclosure.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "or a mixture thereof" refers to "or a mixture of two or more", for example, "the diluent is selected from microcrystalline cellulose, mannitol, lactose, sucrose, starch, pregelatinized starch, dextrin or a mixture thereof", i.e., "the diluent is selected from one or a mixture of two or more of microcrystalline cellulose, mannitol, lactose, sucrose, starch, pregelatinized starch, dextrin".

The excipients used herein may be specific types commonly used in the art. For example, the microcrystalline cellulose that may be used includes, but is not limited to, PH101, PH102, PH103, or PH105. For example, the pregelatinized starch that may be used includes, but is not limited to, Starch1500, Spress B820, or Unipure WG220. For example, the sodium carboxymethyl starch that may be used includes, but is not limited to, type A, or type B. For example, the hydroxypropyl methylcellulose that may be used includes, but is not limited to, E3, E5, or E6. For example, the colloidal silicon dioxide (colloidal silica) that may be used includes, but is not limited to, Pharma 200, AEROSIL 200, or AEROSIL 300. Those skilled in the art may either select the specific type as needed or may select by reference to the prior art such as the *Handbook of Pharmaceutical Excipients* (6th Edition) edited by Raymond C Rowe et al. or the *Extra Pharmaceutical Necessities* (2nd Edition) edited by Luo Mingsheng et al.

The term "bulk density" refers to the bulk packing density measured after the powder freely fills a standard container, i.e., the mass per unit volume of the powder when loosely packed, calculated by mass/volume and represented by g/mL. This may be measured by using methods or equipment commonly used in the art, such as a powder flowability tester BEP2.

The term "tap density" refers to the mass per unit volume of the powder after being vibrated and compacted, calculated by mass/volume and represented by g/mL. This may be measured by using methods or equipment commonly used in the art, such as a packing density tester SOTAX TD1.

The term "Hausner ratio" refers to the ratio calculated by the tap density/bulk density.

The term "particle size distribution" refers to the percentage of particles with different particle sizes of a powder in the total amount of particles (weight distribution). The relevant parameters of the particle size distribution may be measured by using methods or equipment commonly used in the art, such as a vibration sieve instrument AS200, a mechanical sieving method.

Pharmaceutical Composition of the Present Application

The present application provides a solid pharmaceutical composition, which comprises a compound of formula I, a diluent, a binder, a disintegrant, and a lubricant,

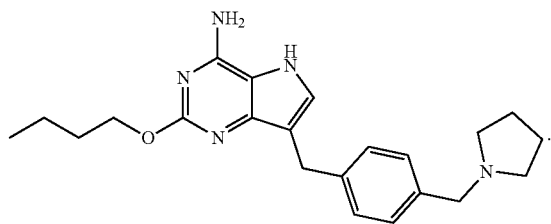

I

The compound of formula I, 2-butoxy-7-(4-(pyrrolidin-1-ylmethyl)benzyl)-5H-pyrrolo[3,2-d]pyrimidin-4-amine, is a TLR7 agonist, and can be used to treat or prevent viral infections.

In some embodiments, the dosage form of the solid pharmaceutical composition may be selected from a powder, a granule, a tablet, a capsule, a pill, a pellet, a dispersion and an inhalable powder, preferably, a tablet.

In some embodiments, the solid pharmaceutical composition may be prepared by a direct compression method.

In some embodiments, the mixture comprising the compound of formula I and the diluent is not subjected to milling during the preparation process of the solid pharmaceutical composition. In some embodiments, the mixture comprising the compound of formula I and the diluent of microcrystalline cellulose or pregelatinized starch is not subjected to milling during the preparation process of the solid pharmaceutical composition. In some embodiments, the mixture comprising the compound of formula I and the diluent of pregelatinized starch is not subjected to milling during the preparation process of the solid pharmaceutical composition. The solid pharmaceutical composition disclosed herein can have excellent homogeneity, stability and dissolution properties without being subjected to such a milling step.

In some embodiments, the solid pharmaceutical composition is a pharmaceutical composition in unit dose. In one embodiment, the mass of the compound of formula I in the composition per unit dose is 0.01 mg-10 mg. In some embodiments, the mass of the compound of formula I in the composition per unit dose is 0.01 mg, 0.02 mg, 0.03 mg, 0.04 mg, 0.05 mg, 0.06 mg, 0.07 mg, 0.08 mg, 0.09 mg, 0.10 mg, 0.20 mg, 0.30 mg, 0.40 mg, 0.50 mg, 0.60 mg, 0.70 mg, 0.80 mg, 0.90 mg, 1.0 mg, 1.5 mg, 2.0 mg, 2.5 mg, 3.0 mg, 3.5 mg, 4.0 mg, 5.0 mg, 6.0 mg, 7.0 mg, 8.0 mg, 9.0 mg, or 10.0 mg; or a range of any two of the foregoing values as endpoints. In some embodiments, the mass of the compound of formula I in the composition per unit dose is 0.02 mg-8.0 mg, 0.03 mg-6.0 mg, 0.04 mg-4.0 mg, or 0.05 mg-2.0 mg.

In some embodiments, the amount of the compound of formula I of the solid pharmaceutical composition is selected from 0.01%-10% wt. In some embodiments, the amount of the compound of formula I is selected from the group consisting of 0.01% wt, 0.02% wt, 0.03% wt, 0.04% wt, 0.05% wt, 0.06% wt, 0.07% wt, 0.08% wt, 0.09% wt, 0.10% wt, 0.15% wt, 0.20% wt, 0.235% wt, 0.25% wt, 0.30% wt, 0.35% wt, 0.40% wt, 0.45% wt, 0.50% wt, 0.55% wt, 0.59% wt, 0.60% wt, 0.65% wt, 0.70% wt, 0.75% wt, 0.80% wt, 0.85% wt, 0.90% wt, 0.95% wt, 1.00% wt, 1.20% wt, 1.40% wt, 1.60% wt, 1.80% wt, 2.00% wt, 2.00% wt, 2.20% wt, 2.35% wt, 2.40% wt, 2.60% wt, 2.80% wt, 3.00% wt, 3.50% wt, 4.00% wt, 4.50% wt, 5.00% wt, 6.00% wt, 7.00% wt, 8.00% wt, 9.00% wt and 10% wt; and a range of any two of the foregoing values as endpoints. In some embodiments, the amount of the compound of formula I is preferably selected from 0.02%-8.0% wt, 0.03%-6.0% wt, 0.04%-4.0% wt, 0.05%-3.0% wt, 0.05%-2.6% wt, 0.06%-3.0% wt, 0.06%-2.6% wt, and 0.06%-2.4% wt. In some embodiments, the amount of the compound of formula I is selected from 0.06%-2.4% wt.

In some embodiments, the diluent is selected from the group consisting of microcrystalline cellulose, mannitol, lactose, sucrose, starch, pregelatinized starch, dextrin, and a mixture thereof; in some embodiments, the diluent is selected from the group consisting of microcrystalline cellulose, mannitol, lactose, pregelatinized starch, and a mixture thereof; in some embodiments, the diluent is selected from the group consisting of microcrystalline cellulose, pregelatinized starch, and a mixture thereof.

In some embodiments, the amount of the diluent is selected from 50% wt or more. In some embodiments, the amount of the diluent is selected from 55% wt or more. In some embodiments, the amount of the diluent is selected from 60% wt or more. In some embodiments, the amount of the diluent is selected from 65% wt or more. In some embodiments, the amount of the diluent is selected from 70% wt or more. In some embodiments, the amount of the diluent is selected from 75% wt or more. In some embodiments, the amount of the diluent is selected from 80% wt or more. In some embodiments, the amount of the diluent is selected from 85% wt or more. In some embodiments, the amount of the diluent is selected from the group consisting of 50% wt, 55% wt, 60% wt, 65% wt, 70% wt, 75% wt, 80% wt, 81% wt, 82% wt, 83% wt, 84% wt, 85% wt, 86% wt, 87% wt, 88% wt, 89% wt, 90% wt, 91% wt, 92% wt, 93% wt, 94% wt, 95% wt, 96% wt, 97% wt, and 98% wt; and a range of any two of the foregoing values as endpoints. In some embodiments, the amount of the diluent is selected from the group consisting of 80%-98% wt, 81%-98% wt, 82%-98% wt, 83%-97% wt, 84%-97% wt, 85%-97% wt, 86%-96% wt, 87%-96% wt, and 88%-96% wt. In some embodiments, the amount of the diluent is selected from 88%-96% wt.

In some embodiments, the diluent comprises microcrystalline cellulose, and the amount of the microcrystalline cellulose is selected from 30%-90% wt. In some embodiments, the amount of the microcrystalline cellulose is selected from the group consisting of 30% wt, 35% wt, 40% wt, 42% wt, 44% wt, 46% wt, 48% wt, 50% wt, 52% wt, 54% wt, 56% wt, 58% wt, 60% wt, 62% wt, 64% wt, 66% wt, 68% wt, 70% wt, 71% wt, 72% wt, 73% wt, 74% wt, 76% wt, 78% wt, 80% wt, 85% wt, and 90% wt; and a range of any two of the foregoing values as endpoints. In some embodiments, the amount of the microcrystalline cellulose is selected from the group consisting of 40%-90% wt, 46%-90% wt, 50%-85% wt, 56%-85% wt, 60%-80% wt, 62%-78% wt, 64%-76% wt, and 66%-74% wt. In some embodiments, the amount of the microcrystalline cellulose is selected from 66%-74% wt.

In some embodiments, the diluent comprises pregelatinized starch, and the amount of the pregelatinized starch is selected from 5%-35% wt. In some embodiments, the amount of the pregelatinized starch is selected from the group consisting of 5% wt, 8% wt, 10% wt, 11% wt, 12% wt, 13% wt, 14% wt, 15% wt, 16% wt, 17% wt, 18% wt, 19% wt, 20% wt, 21% wt, 22% wt, 23% wt, 24% wt, 25% wt, 26% wt, 27% wt, 28% wt, 29% wt, 30% wt, 32% wt, and 35% wt; and a range of any two of the foregoing values as endpoints. In some embodiments, the amount of the pregelatinized starch is selected from the group consisting of 8%-32% wt, 10%-30% wt, 11%-29% wt, 12%-28% wt, 13%-27% wt, 14%-26% wt, 15%-25% wt, 16%-24% wt, 17%-23% wt, and 18%-23% wt. In some embodiments, the amount of the pregelatinized starch is selected from 18%-23% wt.

In some embodiments, the diluent is microcrystalline cellulose and pregelatinized starch. The total amount of the microcrystalline cellulose and the pregelatinized starch is as described above for the amount of the diluent, e.g., 50% wt or more, and other ranges or point values. The amount of both the microcrystalline cellulose and the pregelatinized starch is as described above, e.g., 30%-90% wt of microcrystalline cellulose, 5%-35% wt of pregelatinized starch, and other ranges or point values, respectively.

In some embodiments, the disintegrant is selected from the group consisting of sodium carboxymethyl starch, dry starch, hydroxyethyl methylcellulose, carboxymethylcellulose sodium, carboxymethylcellulose calcium, croscarmellose sodium, low-substituted hydroxypropyl methylcellulose, crospovidone, sodium dodecyl sulfate, magnesium dodecyl sulfate, and a mixture thereof. In some embodiments, the disintegrant is selected from the group consisting of sodium carboxymethyl starch, croscarmellose sodium, and a mixture thereof. In some embodiments, the disintegrant is sodium carboxymethyl starch.

In some embodiments, the amount of the disintegrant is selected from 1.0%-7.0% wt. In some embodiments, the amount of the disintegrant is selected from the group consisting of 1.0% wt, 1.2% wt, 1.4% wt, 1.6% wt, 1.8% wt, 2.0% wt, 2.2% wt, 2.4% wt, 2.6% wt, 2.8% wt, 3.0% wt, 3.2% wt, 3.4% wt, 3.6% wt, 3.8% wt, 4.0% wt, 4.2% wt, 4.4% wt, 4.6% wt, 4.8% wt, 5.0% wt, 5.2% wt, 5.4% wt, 5.6% wt, 5.8% wt, 6.0% wt, 6.2% wt, 6.4% wt, 6.6% wt, 6.8% wt, and 7.0% wt; and a range of any two of the foregoing values as endpoints. In some embodiments, the amount of the disintegrant is selected from the group consisting of 1.2%-6.8% wt, 1.4%-6.6% wt, 1.6%-6.4% wt, 1.8%-6.2% wt, 2.0%-6.0% wt, 2.2%-5.8% wt, 2.4%-5.6% wt, 2.6%-5.4% wt, 2.8%-5.2% wt, 3.0%-5.0% wt, 3.2%-4.8% wt, 3.4%-4.6% wt, 3.6%-4.4% wt, and 3.8%-4.2% wt. In some embodiments, the amount of the disintegrant is 3.8%-4.2% wt.

In some embodiments, the binder is selected from the group consisting of hydroxypropyl methylcellulose (HPMC), carboxymethylcellulose (CMC), carboxymethylcellulose sodium (CMC-Na), ethylcellulose (EC), methylcellulose (MC), hydroxypropylcellulose (HPC), low-substituted hydroxypropylcellulose (L-HPC), gelatin, polyvinylpyrrolidone (PVP), partially hydrolyzed starch, pregelatinized starch, glucose, polyethylene glycol (PEG), polyvinyl alcohol, and a mixture thereof; in some embodiments, the binder is selected from the group consisting of hydroxypropyl methylcellulose (HPMC), carboxymethylcellulose (CMC), carboxymethylcellulose sodium (CMC-Na), ethylcellulose (EC), methylcellulose (MC), hydroxypropylcellulose (HPC), low-substituted hydroxypropylcellulose (L-HPC), polyvinylpyrrolidone, and a mixture thereof; in some embodiments, the binder is hydroxypropyl methylcellulose.

In some embodiments, the amount of the binder is selected from 0.1%-5% wt. In some embodiments, the amount of the binder is selected from the group consisting of 0.1% wt, 0.2% wt, 0.3% wt, 0.4% wt, 0.5% wt, 0.6% wt, 0.7% wt, 0.8% wt, 0.9% wt, 1.0% wt, 1.1% wt, 1.2% wt, 1.3% wt, 1.4% wt, 1.5% wt, 1.6% wt, 1.7% wt, 1.8% wt, 1.9% wt, 2.0% wt, 2.1% wt, 2.2% wt, 2.3% wt, 2.4% wt, 2.5% wt, 2.6% wt, 2.7% wt, 2.8% wt, 2.9% wt, 3.0% wt, 3.2% wt, 3.4% wt, 3.6% wt, 3.8% wt, 4.0% wt, 4.2% wt, 4.4% wt, 4.6% wt, 4.8% wt, and 5.0% wt; and a range of any two of the foregoing values as endpoints. In some embodiments, the amount of the binder is selected from the group consisting of 0.1%-3.0% wt, 0.1%-2.8% wt, 0.1%-2.6% wt, 0.1%-2.4% wt, 0.1%-2.2% wt, 0.1%-2.0% wt, 0.2%-3.0% wt, 0.2%-2.8% wt, 0.2%-2.6% wt, 0.2%-2.4% wt, 0.2%-2.2% wt, 0.2%-2.0% wt, 0.2%-1.9% wt, 0.3%-1.8% wt, 0.4%-1.7% wt, 0.5%-1.6% wt, 0.6%-1.5% wt, 0.7%-1.4% wt, and 0.8%-1.2% wt. In some embodiments, the amount of the binder is 0.8%-1.2% wt.

In some embodiments, the lubricant is selected from the group consisting of magnesium stearate, colloidal silicon dioxide, talc, polyethylene glycol 4000, polyethylene glycol 6000, stearic acid, sodium stearyl fumarate, sodium dodecyl sulfate, and a mixture thereof. In some embodiments, the lubricant is selected from the group consisting of magnesium stearate, colloidal silicon dioxide, sodium dodecyl sulfate, and a mixture thereof. In some embodiments, the lubricant is selected from the group consisting of magnesium stearate, colloidal silicon dioxide, and a mixture thereof.

In some embodiments, the amount of the lubricant is selected from 0.1%-5% wt. In some embodiments, the amount of the lubricant is selected from the group consisting of 0.1% wt, 0.2% wt, 0.3% wt, 0.4% wt, 0.5% wt, 0.6% wt, 0.7% wt, 0.8% wt, 0.9% wt, 1.0% wt, 1.1% wt, 1.2% wt, 1.3% wt, 1.4% wt, 1.5% wt, 1.6% wt, 1.7% wt, 1.8% wt, 1.9% wt, 2.0% wt, 2.1% wt, 2.2% wt, 2.3% wt, 2.4% wt, 2.5% wt, 2.6% wt, 2.7% wt, 2.8% wt, 2.9% wt, 3.0% wt, 3.2% wt, 3.4% wt, 3.6% wt, 3.8% wt, 4.0% wt, 4.2% wt, 4.4% wt, 4.6% wt, 4.8% wt, and 5.0% wt; and a range of any two of the foregoing values as endpoints. In some embodiments, the amount of the lubricant is selected from the group consisting of 0.1%-3.0% wt, 0.1%-2.8% wt, 0.1%-2.6% wt, 0.1%-2.4% wt, 0.1%-2.2% wt, 0.1%-2.0% wt, 0.2%-3.0% wt, 0.2%-2.8% wt, 0.2%-2.6% wt, 0.2%-2.4% wt, 0.2%-2.2% wt, 0.2%-2.0% wt, 0.2%-1.9% wt, 0.3%-1.8% wt, 0.4%-1.7% wt, 0.5%-1.6% wt, 0.6%-1.5% wt, 0.7%-1.4% wt, 0.8%-1.2% wt, and 0.9%-1.1% wt. In some embodiments, the amount of the lubricant is 0.8%-1.2% wt.

In some embodiments, the lubricant comprises colloidal silicon dioxide, and the amount of the colloidal silicon dioxide is selected from 0.05%-3.0% wt. In some embodiments, the amount of the colloidal silicon dioxide is selected from the group consisting of 0.05% wt, 0.06% wt, 0.07% wt, 0.08% wt, 0.09% wt, 0.10% wt, 0.15% wt, 0.20% wt, 0.25% wt, 0.30% wt, 0.35% wt, 0.40% wt, 0.45% wt, 0.50% wt, 0.55% wt, 0.60% wt, 0.65% wt, 0.70% wt, 0.75% wt, 0.80% wt, 0.85% wt, 0.90% wt, 0.95% wt, 1.0% wt, 1.1% wt, 1.2% wt, 1.3% wt, 1.4% wt, 1.5% wt, 1.6% wt, 1.7% wt, 1.8% wt, 1.9% wt, 2.0% wt, 2.2% wt, 2.4% wt, 2.6% wt, 2.8% wt, and 3.0% wt, and a range of any two of the foregoing values as endpoints. In some embodiments, the amount of the colloidal silicon dioxide is selected from the group consisting of 0.05%-2.6% wt, 0.05%-2.2% wt, 0.05%-1.9% wt, 0.05%-1.8% wt, 0.06%-1.7% wt, 0.06%-1.6% wt, 0.07%-1.5% wt, 0.07%-1.4% wt, 0.08%-1.3% wt, 0.08%-1.2% wt, 0.09%-1.1% wt, 0.09%-1.0% wt, 0.10%-0.90% wt, 0.15%-0.85% wt, 0.20%-0.80% wt, 0.25%-0.75% wt, 0.30%-0.70% wt, 0.35%-0.65% wt, 0.40%-0.60% wt, and 0.45%-0.55% wt.

In some embodiments, the amount of the colloidal silicon dioxide is 0.45%-0.55% wt.

In some embodiments, the lubricant comprises magnesium stearate, and the amount of the magnesium stearate is selected from 0.05%-3.0% wt. In some embodiments, the amount of the magnesium stearate is selected from the group consisting of 0.05% wt, 0.06% wt, 0.07% wt, 0.08% wt, 0.09% wt, 0.10% wt, 0.15% wt, 0.20% wt, 0.25% wt, 0.30% wt, 0.35% wt, 0.40% wt, 0.45% wt, 0.50% wt, 0.55% wt, 0.60% wt, 0.65% wt, 0.70% wt, 0.75% wt, 0.80% wt, 0.85% wt, 0.90% wt, 0.95% wt, 1.0% wt, 1.1% wt, 1.2% wt, 1.3% wt, 1.4% wt, 1.5% wt, 1.6% wt, 1.7% wt, 1.8% wt, 1.9% wt, 2.0% wt, 2.2% wt, 2.4% wt, 2.6% wt, 2.8% wt, and 3.0% wt, and a range of any two of the foregoing values as endpoints. In some embodiments, the amount of the magnesium stearate is selected from the group consisting of 0.05%-2.6% wt, 0.05%-2.2% wt, 0.05%-1.9% wt, 0.05%-1.8% wt, 0.06%-1.7% wt, 0.06%-1.6% wt, 0.07%-1.5% wt, 0.07%-1.4% wt, 0.08%-1.3% wt, 0.08%-1.2% wt, 0.09%-1.1% wt, 0.09%-1.0% wt, 0.10%-0.90% wt, 0.15%-0.85% wt, 0.20%-0.80% wt, 0.25%-0.75% wt, 0.30%-0.70% wt, 0.35%-0.65% wt, 0.40%-0.60% wt, and 0.45%-0.55% wt. In some embodiments, the amount of the magnesium stearate is 0.45%-0.55% wt.

In some embodiments, the lubricant is colloidal silicon dioxide and magnesium stearate. The total amount of the colloidal silicon dioxide and the magnesium stearate is as described above for the amount of the lubricant, e.g., 0.1%-5% wt and other ranges or point values. The amount of both the colloidal silicon dioxide and the magnesium stearate is as described above, e.g., 0.05%-3.0% wt of colloidal silicon dioxide, 0.05%-3.0% wt of magnesium stearate, and other ranges or point values, respectively.

Micromeritic Parameters

In some embodiments, the bulk density of the solid pharmaceutical composition disclosed herein is ≤0.50 g/mL, ≤0.49 g/mL, ≤0.48 g/mL, ≤0.47 g/mL, ≤0.46 g/mL, ≤0.45 g/mL, or ≤0.44 g/mL. In some specific embodiments, the bulk density of the solid pharmaceutical composition disclosed herein is 0.30 g/mL-0.50 g/mL. In some embodiments, the bulk density of the solid pharmaceutical composition disclosed herein is 0.30 g/mL, 0.31 g/mL, 0.32 g/mL, 0.33 g/mL, 0.34 g/mL, 0.35 g/mL, 0.36 g/mL, 0.37 g/mL, 0.38 g/mL, 0.39 g/mL, 0.40 g/mL, 0.41 g/mL, 0.42 g/mL, 0.43 g/mL, 0.44 g/mL, 0.45 g/mL, 0.46 g/mL, 0.47 g/mL, 0.48 g/mL, 0.49 g/mL, or 0.50 g/mL; or a range of any two of the foregoing values as endpoints. In some embodiments, the bulk density of the solid pharmaceutical composition disclosed herein is 0.40 g/mL-0.50 g/mL, 0.41 g/mL-0.49 g/mL, 0.42 g/mL-0.48 g/mL, 0.43 g/mL-0.47 g/mL, or 0.44 g/mL-0.46 g/mL.

In some embodiments, the tap density of the solid pharmaceutical composition disclosed herein is ≤0.65 g/mL, ≤0.64 g/mL, ≤0.63 g/mL, ≤0.62 g/mL, ≤0.61 g/mL, ≤0.60 g/mL, or ≤0.59 g/mL. In some embodiments, the tap density of the solid pharmaceutical composition disclosed herein is 0.50 g/mL-0.65 g/mL. In some embodiments, the tap density of the solid pharmaceutical composition disclosed herein is 0.50 g/mL, 0.51 g/mL, 0.52 g/mL, 0.53 g/mL, 0.54 g/mL, 0.55 g/mL, 0.56 g/mL, 0.57 g/mL, 0.58 g/mL, 0.59 g/mL, 0.60 g/mL, 0.61 g/mL, 0.62 g/mL, 0.63 g/mL, 0.64 g/mL, or 0.65 g/mL; or a range of any two of the foregoing values as endpoints. In some embodiments, the tap density of the solid pharmaceutical composition disclosed herein is 0.52 g/mL-0.64 g/mL, 0.54 g/mL-0.63 g/mL, 0.56 g/mL-0.62 g/mL, or 0.58 g/mL-0.61 g/mL.

In some embodiments, the Hausner ratio of the solid pharmaceutical composition disclosed herein is 1.31-1.40. In some embodiments, the Hausner ratio of the solid pharmaceutical composition disclosed herein is 1.31, 1.32, 1.33, 1.34, 1.35, 1.36, 1.37, 1.38, 1.39, or 1.40; or a range of any two of the foregoing values as endpoints. In some embodiments, the Hausner ratio of the solid pharmaceutical composition disclosed herein is 1.31-1.38, 1.32-1.37, 1.32-1.36, 1.33-1.36, or 1.33-1.35.

Particle Size Distribution

The solid pharmaceutical composition disclosed herein features particle size distribution. The particle size in the solid pharmaceutical composition disclosed herein is mainly distributed within the range of less than 75 μm. In some embodiments, ≥50%, ≥51%, ≥52%, ≥53%, ≥55%, ≥55%, ≥56%, ≥57%, ≥58%, ≥59%, ≥60%, ≥61%, ≥62%, ≥63%, ≥66%, ≥65%, ≥66%, ≥67% or ≥68% of the particles in the solid pharmaceutical composition disclosed herein have a size of less than 75 μm. In some embodiments, 50%-80% of the particles in the solid pharmaceutical composition disclosed herein have a size of less than 75 μm. In some embodiments, 50%, 51%, 52%, 53%, 55%, 55%, 56%, 57%, 58%, 59%, 60%, 61%, 62%, 63%, 66%, 65%, 66%, 67%, 68%, 69%, 70%, 71%, 72%, 73%, 77%, 75%, 77%, 77%, 78%, 79% or 80% of the particles in the solid pharmaceutical composition disclosed herein have a size of less than 75 μm; or the particles, with the amount within a range of any two of the foregoing values as endpoints, have a size of less than 75 μm. In some embodiments, 56%-80%, 58%-78%, 60%-76%, 62%-74%, 64%-72% or 66%-70% of the particles in the solid pharmaceutical composition disclosed herein have a size of less than 75 μm. The above ratio is the weight distribution (i.e., by weight).

In some embodiments, 24%-40% of the particles in the solid pharmaceutical composition disclosed herein have a size of 75 μm-150 μm. In some embodiments, 24%, 25%, 26%, 27%, 28%, 29%, 30%, 31%, 32%, 33%, 34%, 35%, 36%, 37%, 38%, 39% or 40% of the particles in the solid pharmaceutical composition disclosed herein have a size of 75 μm-150 μm; or the particles, with the amount within a range of any two of the foregoing values as endpoints, have a size of 75 μm-150 μm. In some embodiments, 24%-40%, 25%-38%, 26%-36%, 27%-34% or 28%-32% of the particles in the solid pharmaceutical composition disclosed herein have a size of 75 μm-150 μm. The above ratio is the weight distribution (i.e., by weight).

Only a small amount of particles in the pharmaceutical composition disclosed herein have a size of more than 150 μm. In some embodiments, ≤10%, ≤9%, ≤8%, ≤7%, ≤6%, ≤5%, ≤4%, ≤3%, ≤2% or ≤1% of the particles in the solid pharmaceutical composition disclosed herein have a size of more than 150 μm. In some embodiments, 0.1%-10% of the particles in the solid pharmaceutical composition disclosed herein have a size of more than 150 μm. In some embodiments, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.2%, 3.4%, 3.6%, 3.8%, 4.0%, 4.2%, 4.4%, 4.6%, 4.8%, 5.0%, 5.2%, 5.4%, 5.6%, 5.8%, 6.0%, 6.5%, 7.0%, 7.5%, 8.0%, 8.5%, 9.0%, 9.5% or 10% of the particles in the solid pharmaceutical composition disclosed herein have a size of more than 150 μm, or the particles, with the amount within a range of any two of the foregoing values as endpoints, have a size of more than 150 μm. In some embodiments, 0.1%-5.0%, 0.1%-4.8%, 0.2%-4.6%, 0.2%-4.4%, 0.3%-4.2%, 0.3%-4.0%, 0.4%-3.8%, 0.4%-3.6%, 0.5%-3.4%, 0.5%-3.2%, 0.6%-3.0%, 0.7%-2.8%, 0.8%-2.6%, 0.9%-2.4%, 1.0%-2.2%, 1.2%-2.0% or 1.4%-1.8% of the particles in the solid pharmaceutical composition disclosed herein have a size of more than 150 μm. The above ratio is the weight distribution (i.e., by weight).

It will also be appreciated by those skilled in the art that, in addition to the compound of formula I described above as an active ingredient, together with the diluent, the binder, the disintegrant and the lubricant, other pharmaceutically acceptable excipients or additives may be included in the pharmaceutical composition disclosed herein as desired, such as, but not limited to, antioxidants, preservatives, colorants and flavouring agents, the selection and amount of which can be adjusted by those skilled in the art according to actual needs.

The pharmaceutical compositions disclosed herein have high purity (i.e., low impurity content). In one embodiment, the pharmaceutical composition disclosed herein has a total impurity content of 0.5% or less, preferably 0.45% or less, more preferably 0.4% or less, and in particular, preferably 0.3% or less.

The pharmaceutical composition disclosed herein has excellent stability. In one embodiment, the pharmaceutical composition disclosed herein has a total impurity content of 1.2% or less, preferably 1.1% or less, more preferably 1% or less, for example, 0.9% or less, 0.8% or less, 0.7% or less, 0.6% or less, 0.5% or less, 0.4% or less, under an accelerated condition for 6 months (40° C.±2° C., RH75%±5%).

The pharmaceutical composition disclosed herein has excellent dissolution properties. In one embodiment, the pharmaceutical composition disclosed herein may have a dissolution of 90% or higher after 20 min.

The pharmaceutical composition disclosed herein has excellent mixing homogeneity, with its homogeneity meeting the limit requirements (A+2.2S≤15.0, see examples) and being much lower than the upper limit of the requirements.

Preparation Method

In another aspect, the present application provides a method for preparing the solid pharmaceutical composition of the compound of formula I disclosed herein, which comprises a direct compression method.

In one embodiment, the method for preparing the solid pharmaceutical composition of the compound of formula I disclosed herein comprises:

1) mixing the compound of formula I with part or all of the diluent and, optionally present, at least one of the binder, the disintegrant and the lubricant;

2) mixing the resulting mixture obtained in step 1) with the rest of the diluent and at least one of the rest of the binder, the disintegrant and the lubricant;

optionally, 3) mixing the resulting mixture obtained in step 2) with the rest of the excipients; and 4) tableting the resulting mixture obtained in step 2) or step 3).

The selection and amounts of the compound of formula I and excipients such as the diluent, the binder, the disintegrant and the lubricant used in the method are as described above.

It will be appreciated by those skilled in the art that, if all of the diluent is used in step 1), then no remaining diluent is required to be used in step 2).

In one embodiment, the diluent, the binder, the disintegrant and the lubricant may be independently added in portions or at once for mixing. When the excipients such as the diluent, the binder, the disintegrant and the lubricant are added in portions, the proportion of the excipients added in portions can be determined by those skilled in the art as needed.

The preparation method disclosed herein can be carried out by direct compression without the use of (dry) granulation.

The solid pharmaceutical composition obtained using the preparation method disclosed herein may have excellent homogeneity, stability and dissolution properties.

In an exemplary embodiment, the preparation method disclosed herein or the direct compression method may comprise: 1) preparing the compound of formula I, the diluent, the disintegrant, the binder and the lubricant into a mixture; and 2) tableting. In some embodiments, the direct compression method comprises: 1) preparing the compound of formula I, the diluent, the disintegrant and the binder into a mixture; 2) preparing the resulting mixture obtained in step 1) and the lubricant into a mixture; and 3) tableting. In another embodiment, the direct compression method comprises: 1) preparing the compound of formula I and part of the diluent into a mixture; 2) preparing the resulting mixture obtained in step 1) and the rest of the diluent, the disintegrant and the binder into a mixture; 3) preparing the resulting mixture obtained in step 2) and the lubricant into a mixture; and 4) tableting. In an alternative embodiment, the direct compression method comprises: 1) preparing the compound of formula I and part of the diluent into a mixture; 2) preparing the resulting mixture obtained in step 1) and the rest of the diluent, the disintegrant and the binder into a mixture; 3) preparing the resulting mixture obtained in step 2) and part of the lubricant into a mixture; 4) preparing the resulting mixture obtained in step 3) and the rest of the lubricant into a mixture; and 5) tableting. In other embodiments, the direct compression method comprises: 1) preparing the compound of formula I and the diluent into a mixture; 2) preparing the resulting mixture obtained in step 1) and the disintegrant and the binder into a mixture; 3) preparing the resulting mixture obtained in step 2) and a lubricant into a mixture; and 4) tableting. In still other embodiments, the direct compression method comprises: 1) preparing the compound of formula I and the diluent into a mixture; 2) preparing the resulting mixture obtained in step 1) and the disintegrant and the binder into a mixture; 3) preparing the resulting mixture obtained in step 2) and part of the lubricant into a mixture; 4) preparing the resulting mixture obtained in step 3) and the rest of the lubricant into a mixture; and 5) tableting. The active ingredient and the excipients are added according to the required proportion of the pharmaceutical composition. When the excipients are added in portions, the proportion of the excipients added in portions can be determined by those skilled in the art as needed.

In some embodiments, the mixture comprising the compound of formula I and the diluent is not subjected to milling in the method for preparing the solid pharmaceutical composition of the compound of formula I. In some embodiments, the mixture comprising the compound of formula I and the diluent of microcrystalline cellulose or pregelatinized starch is not subjected to milling in the method for preparing the solid pharmaceutical composition of the compound of formula I. In some embodiments, the mixture comprising the compound of formula I and the diluent of pregelatinized starch is not subjected to milling in the method for preparing the solid pharmaceutical composition of the compound of formula I. The solid pharmaceutical composition disclosed herein can have excellent homogeneity, stability and dissolution properties without being subjected to such a milling step.

The tableting parameters may be selected by those skilled in the art according to actual needs.

In an exemplary embodiment, the parameters used herein are 6-mm shallow concave punch and hardness of 6 Kp-9 Kp.

EMBODIMENTS OF THE PRESENT INVENTION

In some embodiments of the present application, the solid pharmaceutical composition disclosed herein comprises:

A) In some embodiments, the solid pharmaceutical composition comprises:
0.02%-8.0% wt of the compound of formula I;
50% wt or more of microcrystalline cellulose, mannitol, lactose, pregelatinized starch, or a mixture thereof;
1.0%-7.0% wt of sodium carboxymethyl starch, croscarmellose sodium, or a mixture thereof;
0.1%-5% wt of hydroxypropyl methylcellulose, carboxymethylcellulose, carboxymethylcellulose sodium, ethylcellulose, methylcellulose, hydroxypropylcellulose, low-substituted hydroxypropylcellulose, polyvinylpyrrolidone, or a mixture thereof; and
0.1%-5% wt of magnesium stearate, colloidal silicon dioxide, sodium dodecyl sulfate, or a mixture thereof.

B) In some embodiments, the solid pharmaceutical composition comprises:
0.03%-7.0% wt of the compound of formula I;
50% wt or more of microcrystalline cellulose, pregelatinized starch, or a mixture thereof;
1.0%-7.0% wt of sodium carboxymethyl starch;
0.1%-5% wt of hydroxypropyl methylcellulose; and
0.1%-5% wt of magnesium stearate, colloidal silicon dioxide, or a mixture thereof.

C) In some embodiments, the solid pharmaceutical composition comprises:
0.03%-6.0% wt of the compound of formula I;
60% wt or more of microcrystalline cellulose, mannitol, lactose, pregelatinized starch, or a mixture thereof;
1.6%-6.4% wt of sodium carboxymethyl starch, croscarmellose sodium, or a mixture thereof;
0.1%-2.2% wt of hydroxypropyl methylcellulose, carboxymethylcellulose, carboxymethylcellulose sodium, ethylcellulose, methylcellulose, hydroxypropylcellulose, low-substituted hydroxypropylcellulose, polyvinylpyrrolidone, or a mixture thereof; and
0.1%-2.2% wt of magnesium stearate, colloidal silicon dioxide, sodium dodecyl sulfate, or a mixture thereof.

D) In some embodiments, the solid pharmaceutical composition comprises:
0.04%-5.0% wt of the compound of formula I;
60% wt or more of microcrystalline cellulose, pregelatinized starch, or a mixture thereof;
1.6%-6.4% wt of sodium carboxymethyl starch;
0.1%-2.2% wt of hydroxypropyl methylcellulose; and
0.1%-2.2% wt of magnesium stearate, colloidal silicon dioxide, or a mixture thereof.

E) In some embodiments, the solid pharmaceutical composition comprises:
0.05%-3.5% wt of the compound of formula I;
70% wt or more of microcrystalline cellulose, mannitol, lactose, pregelatinized starch, or a mixture thereof;
2.4%-5.6% wt of sodium carboxymethyl starch, croscarmellose sodium, or a mixture thereof;
0.2%-2.4% wt of hydroxypropyl methylcellulose, carboxymethylcellulose, carboxymethylcellulose sodium, ethylcellulose, methylcellulose, hydroxypropylcellulose, low-substituted hydroxypropylcellulose, polyvinylpyrrolidone, or a mixture thereof; and
0.2%-2.4% wt of magnesium stearate, colloidal silicon dioxide, sodium dodecyl sulfate, or a mixture thereof.

F) In some embodiments, the solid pharmaceutical composition comprises:
0.05%-3.5% wt of the compound of formula I;
70% wt or more of microcrystalline cellulose, pregelatinized starch, or a mixture thereof;
2.4%-5.6% wt of sodium carboxymethyl starch;
0.2%-2.4% wt of hydroxypropyl methylcellulose; and
0.2%-2.4% wt of magnesium stearate, colloidal silicon dioxide, or a mixture thereof.

G) In some embodiments, the solid pharmaceutical composition comprises:
0.05%-2.8% wt of the compound of formula I;
80% wt or more of microcrystalline cellulose, mannitol, lactose, pregelatinized starch, or a mixture thereof;
3.0%-5.0% wt of sodium carboxymethyl starch, croscarmellose sodium, or a mixture thereof;
0.2%-1.9% wt of hydroxypropyl methylcellulose, carboxymethylcellulose, carboxymethylcellulose sodium, ethylcellulose, methylcellulose, hydroxypropylcellulose, low-substituted hydroxypropylcellulose, polyvinylpyrrolidone, or a mixture thereof; and
0.2%-1.9% wt of magnesium stearate, colloidal silicon dioxide, sodium dodecyl sulfate, or a mixture thereof.

H) In some embodiments, the solid pharmaceutical composition comprises:
0.05%-2.8% wt of the compound of formula I;
80% wt or more of microcrystalline cellulose, pregelatinized starch, or a mixture thereof;
3.0%-5.0% wt of sodium carboxymethyl starch;
0.2%-1.9% wt of hydroxypropyl methylcellulose; and
0.2%-1.9% wt of magnesium stearate, colloidal silicon dioxide, or a mixture thereof.

I) In some embodiments, the solid pharmaceutical composition comprises:
0.05%-2.6% wt of the compound of formula I;
82%-98% wt of microcrystalline cellulose, mannitol, lactose, pregelatinized starch, or a mixture thereof;
3.4%-4.6% wt of sodium carboxymethyl starch, croscarmellose sodium, or a mixture thereof; and
0.5%-1.6% wt of hydroxypropyl methylcellulose, carboxymethylcellulose, carboxymethylcellulose sodium, ethylcellulose, methylcellulose, hydroxypropylcellulose, low-substituted hydroxypropylcellulose, polyvinylpyrrolidone, or a mixture thereof; and 0.5%-1.6% wt of magnesium stearate, colloidal silicon dioxide, sodium dodecyl sulfate, or a mixture thereof.

J) In some embodiments, the solid pharmaceutical composition comprises:
0.05%-2.6% wt of the compound of formula I;
82%-98% wt of microcrystalline cellulose, pregelatinized starch, or a mixture thereof;
3.4%-4.6% wt of sodium carboxymethyl starch;
0.5%-1.6% wt of hydroxypropyl methylcellulose; and
0.5%-1.6% wt of magnesium stearate, colloidal silicon dioxide, or a mixture thereof.

K) In some embodiments, the solid pharmaceutical composition comprises:
0.05%-2.6% wt of the compound of formula I;
82%-98% wt of microcrystalline cellulose and pregelatinized starch, including 56%-85% wt of microcrystalline cellulose and 12%-28% wt of pregelatinized starch;
3.4%-4.6% wt of sodium carboxymethyl starch;
0.5%-4.6% wt of hydroxypropyl methylcellulose; and
0.5%-1.6% wt of magnesium stearate and colloidal silicon dioxide, including 0.09%-1.0% wt of magnesium stearate and 0.09%-1.0% wt of colloidal silicon dioxide.

L) In some embodiments, the solid pharmaceutical composition comprises:
0.06%-2.6% wt of the compound of formula I;
85%-97% wt of microcrystalline cellulose, mannitol, lactose or pregelatinized starch, or a mixture thereof.
3.6%-4.4% wt of sodium carboxymethyl starch, croscarmellose sodium, or a mixture thereof;
0.7%-1.4% wt of hydroxypropyl methylcellulose, carboxymethylcellulose, carboxymethylcellulose sodium, ethylcellulose, methylcellulose, hydroxypropylcellulose, low-substituted hydroxypropylcellulose, polyvinylpyrrolidone, or a mixture thereof; and
0.7%-1.4% wt of magnesium stearate, colloidal silicon dioxide, sodium dodecyl sulfate, or a mixture thereof.

M) In some embodiments, the solid pharmaceutical composition comprises:
0.06%-2.6% wt of the compound of formula I;
85%-97% wt of microcrystalline cellulose, pregelatinized starch, or a mixture thereof;
3.6%-4.4% wt of sodium carboxymethyl starch;
0.7%-1.4% wt of hydroxypropyl methylcellulose; and
0.7%-1.4% wt of magnesium stearate, colloidal silicon dioxide, or a mixture thereof.

N) In some embodiments, the solid pharmaceutical composition comprises:
0.06%-2.6% wt of the compound of formula I;
85%-97% wt of microcrystalline cellulose and pregelatinized starch, including 62%-78% wt of microcrystalline cellulose or 15%-25% wt of pregelatinized starch;
3.6%-4.4% wt of sodium carboxymethyl starch;
0.7%-1.4% wt of hydroxypropyl methylcellulose; and
0.7%-1.4% wt of magnesium stearate and colloidal silicon dioxide, including 0.20%-0.80% wt of magnesium stearate and 0.20%-0.80% wt of colloidal silicon dioxide.

O) In some embodiments, the solid pharmaceutical composition comprises:
0.06%-2.4% wt of the compound of formula I;
88%-96% wt of microcrystalline cellulose, mannitol, lactose, pregelatinized starch, or a mixture thereof;
3.8%-4.2% wt of sodium carboxymethyl starch, croscarmellose sodium, or a mixture thereof;
0.8%-1.2% wt of hydroxypropyl methylcellulose, carboxymethylcellulose, carboxymethylcellulose sodium, ethylcellulose, methylcellulose, hydroxypropylcellulose, low-substituted hydroxypropylcellulose, polyvinylpyrrolidone, or a mixture thereof; and
0.8%-1.2% wt of magnesium stearate, colloidal silicon dioxide, sodium dodecyl sulfate, or a mixture thereof.

P) In some embodiments, the solid pharmaceutical composition comprises:
0.06%-2.4% wt of the compound of formula I;
88%-96% wt of microcrystalline cellulose, pregelatinized starch, or a mixture thereof;
3.8%-4.2% wt of sodium carboxymethyl starch;
0.8%-1.2% wt of hydroxypropyl methylcellulose; and
0.8%-1.2% wt of magnesium stearate, colloidal silicon dioxide, or a mixture thereof.

Q) In some embodiments, the solid pharmaceutical composition comprises:
0.06%-2.4% wt of the compound of formula I;
88%-96% wt of microcrystalline cellulose and pregelatinized starch, including 66%-74% wt of microcrystalline cellulose or 18%-23% wt of pregelatinized starch;
3.8%-4.2% wt of sodium carboxymethyl starch;
0.8%-1.2% wt of hydroxypropyl methylcellulose; and
0.8%-1.2% wt of magnesium stearate and colloidal silicon dioxide, including 0.35%-0.65% wt of magnesium stearate and 0.35%-0.65% wt of colloidal silicon dioxide.

In some embodiments, the solid pharmaceutical composition may further comprise a coating agent. In some embodiments, the coating agent is formed from an aqueous film coating composition, wherein the aqueous film coating composition comprises a film-forming polymer, water and/or an alcohol as a carrier, and optionally one or more additives such as additives known in the film coating field. In some embodiments, the coating agent is selected from the group consisting of hydroxypropyl methylcellulose, hydroxypropylcellulose, methylcellulose, ethylcellulose, hydroxyethylcellulose, cellulose acetate phthalate, sodium ethylcellulose sulfate, carboxymethylcellulose, polyvinylpyrrolidone, zein, acrylic polymers (for example, methacrylic acid/methacrylate copolymers, such as methacrylic acid/methyl methacrylate copolymers), and polyvinyl alcohol.

The present application further encompasses the following embodiments:

1. A solid pharmaceutical composition, comprising a compound of formula I, a diluent, a binder, a disintegrant, and a lubricant,

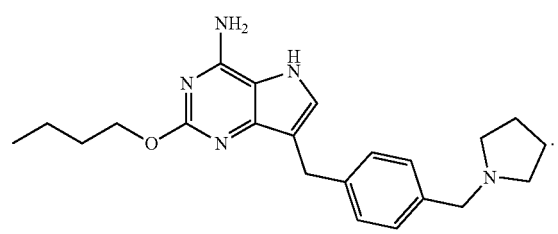

I

2. The solid pharmaceutical composition according to Embodiment 1, wherein the solid pharmaceutical composition is a pharmaceutical composition in unit dose, and the mass of the compound of formula I in the composition per unit dose is 0.01 mg-10 mg.

3. The solid pharmaceutical composition according to Embodiment 1, wherein the amount of the compound of formula I is selected from 0.01%-10% wt.

4. The solid pharmaceutical composition according to Embodiment 1, wherein the diluent is selected from the group consisting of microcrystalline cellulose, mannitol, lactose, sucrose, starch, pregelatinized starch, dextrin, and a mixture thereof; preferably, microcrystalline cellulose, mannitol, lactose, pregelatinized starch, and a mixture thereof; more preferably, microcrystalline cellulose, pregelatinized starch, and a mixture thereof.

5. The solid pharmaceutical composition according to Embodiment 1, wherein the amount of the diluent is selected from 50% wt or more.

6. The solid pharmaceutical composition according to Embodiment 4, wherein the diluent comprises microcrystalline cellulose, and the amount of the microcrystalline cellulose is selected from 30%-90% wt.

7. The solid pharmaceutical composition according to Embodiment 4, wherein the diluent comprises pregelatinized starch, and the amount of the pregelatinized starch is selected from 5%-35% wt.

8. The solid pharmaceutical composition according to Embodiment 4, wherein the diluent is microcrystalline cellulose and pregelatinized starch; preferably, 30%-90% wt of microcrystalline cellulose and 5%-35% wt of pregelatinized starch, and the amount of the diluent is 50% wt or more.

9. The solid pharmaceutical composition according to Embodiment 1, wherein the disintegrant is selected from the group consisting of sodium carboxymethyl starch, dry starch, microcrystalline cellulose, hydroxyethyl methylcellulose, carboxymethylcellulose sodium, carboxymethylcellulose calcium, croscarmellose sodium, low-substituted hydroxypropyl methylcellulose or crospovidone, sodium dodecyl sulfate or magnesium dodecyl sulfate, and a mixture thereof; preferably, sodium carboxymethyl starch, croscarmellose sodium, and a mixture thereof; more preferably, sodium carboxymethyl starch.

10. The solid pharmaceutical composition according to Embodiment 9, wherein the amount of the disintegrant is selected from 1.0%-7.0% wt.

11. The solid pharmaceutical composition according to Embodiment 9, wherein the disintegrant is sodium carboxymethyl starch, and the amount of the sodium carboxymethyl starch is selected from 1.0%-7.0% wt.

12. The solid pharmaceutical composition according to Embodiment 1, wherein the binder is selected from the group consisting of hydroxypropyl methylcellulose, carboxymethylcellulose, carboxymethylcellulose sodium, ethylcellulose, methylcellulose, hydroxypropylcellulose, low-substituted hydroxypropylcellulose, gelatin, polyvinylpyrrolidone, partially hydrolyzed starch, pregelatinized starch, glucose, polyethylene glycol, polyvinyl alcohol, and a mixture thereof; preferably, hydroxypropyl methylcellulose, carboxymethylcellulose, carboxymethylcellulose sodium, ethylcellulose, methylcellulose, hydroxypropylcellulose, low-substituted hydroxypropylcellulose (L-HPC), polyvinylpyrrolidone, and a mixture thereof; more preferably, hydroxypropyl methylcellulose.

13. The solid pharmaceutical composition according to Embodiment 12, wherein the amount of the binder is selected from 0.1%-5% wt.

14. The solid pharmaceutical composition according to Embodiment 12, wherein the binder is hydroxypropyl methylcellulose, and the amount of the hydroxypropyl methylcellulose is selected from 0.1%-5% wt.

15. The solid pharmaceutical composition according to Embodiment 1, wherein the lubricant is selected from the group consisting of magnesium stearate, colloidal silicon dioxide, talc, polyethylene glycol 4000, polyethylene glycol 6000, stearic acid, sodium stearyl fumarate, sodium dodecyl sulfate, and a mixture thereof; preferably, magnesium stearate, colloidal silicon dioxide, sodium dodecyl sulfate, and a mixture thereof; more preferably, magnesium stearate, colloidal silicon dioxide, and a mixture thereof.

16. The solid pharmaceutical composition according to Embodiment 15, wherein the amount of the lubricant is selected from 0.1%-5% wt.

17. The solid pharmaceutical composition according to Embodiment 15, wherein the lubricant comprises colloidal silicon dioxide, and the amount of the colloidal silicon dioxide is selected from 0.05%-3.0% wt.

18. The solid pharmaceutical composition according to Embodiment 15, wherein the lubricant comprises magnesium stearate, and the amount of the magnesium stearate is selected from 0.05%-3.0% wt.

19. The solid pharmaceutical composition according to Embodiment 15, wherein the lubricant is selected from the group consisting of colloidal silicon dioxide and magnesium stearate; preferably, 0.05%-3.0% wt of colloidal silicon dioxide and 0.05%-3.0% wt of magnesium stearate, and the amount of the lubricant is selected from 0.1%-5% wt.

20. The solid pharmaceutical composition according to any one of Embodiments 1-19, comprising:
   0.02%-8.0% wt of the compound of formula I;
   50% wt or more of microcrystalline cellulose, mannitol, lactose, pregelatinized starch, or a mixture thereof;
   1.0%-7.0% wt of sodium carboxymethyl starch, croscarmellose sodium, or a mixture thereof;
   0.1%-5% wt of hydroxypropyl methylcellulose, carboxymethylcellulose, carboxymethylcellulose sodium, ethylcellulose, methylcellulose, hydroxypropylcellulose, low-substituted hydroxypropylcellulose, polyvinylpyrrolidone, or a mixture thereof; and
   0.1%-5% wt of magnesium stearate, colloidal silicon dioxide, sodium dodecyl sulfate, or a mixture thereof.

21. The solid pharmaceutical composition according to any one of Embodiments 1-20, further comprising a coating agent.

22. The solid pharmaceutical composition according to any one of Embodiments 1-20, wherein the dosage form of the solid pharmaceutical composition may be selected from a powder, a granule, a tablet, a capsule, a pill, a pellet, a dispersion and an inhalable powder, preferably, a tablet.

23. The solid pharmaceutical composition according to any one of Embodiments 1-22, wherein the solid pharmaceutical composition is prepared by a direct compression method.

24. The solid pharmaceutical composition according to Embodiment 23, wherein the direct compression method comprises the following process: 1) preparing the compound of formula I, the diluent, the disintegrant, the binder and the lubricant into a mixture; and 2) tableting.

25. A method for preparing the solid pharmaceutical composition of the compound of formula I according to any one of Embodiments 1-22, wherein the method is selected from a direct compression method.

26. The method according to Embodiment 25, wherein the direct compression method comprises the following process: 1) preparing the compound of formula I, the diluent, the disintegrant, the binder and the lubricant into a mixture; and 2) tableting.

27. Use of the solid pharmaceutical composition of the compound of formula I according to any one of Embodiments 1-22 for the manufacture of a medicament for the treatment of a disease associated with TLR7.

28. The use according to Embodiment 27, wherein the disease benefiting from the agonism of TLR7 is selected from a viral infectious disease; preferably, the viral infectious disease is selected from the group consisting of hepatitis B and hepatitis C.

Therapeutic or Prophylactic Methods and Use

In still another aspect, the present application provides use of the solid pharmaceutical composition of the compound of formula I for the manufacture of a medicament for the treatment or prevention of a disease associated with TLR7. In yet another aspect, the present application provides a solid pharmaceutical composition of the compound of formula I for use in treating or preventing a disease associated with TLR7. In a further aspect, the present application further provides a method for treating or preventing a disease associated with TLR7, which comprises administering to a subject in need thereof the solid pharmaceutical composition of the compound of formula I disclosed herein. The subject is, for example a mammal, preferably a human.

In some embodiments, the disease associated with TLR7 is selected from a viral infectious disease; preferably, the viral infectious disease is selected from the group consisting of hepatitis B and hepatitis C.

Beneficial Effects

During the development of the solid pharmaceutical composition of the compound of formula I, the adhesion of the particles may cause repulsion between the particles, resulting in mixing non-homogeneity, and during the prolonged mixing, the phenomenon is increasingly evident along with charge build-up caused by friction, and accompanied by lump formation. This may lead to large differences in the content of active ingredients in a unit preparation, affecting the efficacy of the medicament. In addition, when the preparation is small in specification, the toxic and side effects are easily aggravated due to non-homogeneity of the content of the active ingredients. Therefore, in the process of developing the solid pharmaceutical composition of the compound of formula I, the above problems need to be solved so as to obtain a pharmaceutical composition with good homogeneity, solubility and stability for clinical use.

It is found in the present application that the solid pharmaceutical composition disclosed herein has specific micromeritic parameters and particle size distribution characteristics, shows excellent homogeneity, stability and dissolution properties, and has good pharmacokinetic properties, which is suitable for clinical use. The solid pharmaceutical composition described herein prepared by powder direct compression has excellent homogeneity, stability and dissolution properties, and has good pharmacokinetic properties, which is suitable for clinical use. In addition, when the compound of formula I and the diluent are not co-milled during the preparation process, the prepared solid pharmaceutical composition described herein has excellent homogeneity, stability and dissolution properties, and has good pharmacokinetic properties, which is suitable for clinical use.

EXAMPLES

The present application will be described illustratively with reference to specific examples; however, these examples are not intended to limit the scope of the present application. The excipients and reagents used are all commercially available products. For example, the excipients used may be available from Colorcon, Dow Chemical, FMC Corporation, and the like. The compound of formula I is commercially available or may be synthesized using the method described in WO2016/023511. In the examples of the specification, unless otherwise stated, the compound of formula I used is in a free base form. The instruments and equipment used may be the preparation equipment commonly used in the art, such as a dry-wet granulator U5 and a hopper mixer HBD-5.

Example 1: Powder Direct Compression

The pharmaceutical composition is prepared using a (powder) direct compression method. The ingredients and proportions used are given in the following table.

| Components | | mg/tablet | Percentage % (w/w) |
|---|---|---|---|
| Compound of formula I | Active ingredient | 0.05 | 0.06 |
| Microcrystalline cellulose | Diluent | 61.85 | 72.76 |
| Pregelatinized starch | Diluent | 18 | 21.18 |
| Sodium carboxymethyl starch | Disintegrant | 3.4 | 4.00 |
| Hydroxypropyl methylcellulose | Binder | 0.85 | 1.00 |
| Colloidal silicon dioxide | Lubricant | 0.425 | 0.50 |
| Magnesium stearate | Lubricant | 0.425 | 0.50 |
| Total amount | | 85 | 100 |

Preparation Method

1. Pretreatment: taking the compound of formula I, then taking pregelatinized starch with a weight ratio of the compound of formula I and the pregelatinized starch being 1:20 (the compound of formula I: pregelatinized starch, w/w=1:20), manually mixing the two, and sieving the mixture with a 60-mesh sieve to obtain a pre-treated material for later use;

2. Premixing: mixing the pre-treated material with the rest predetermined amount of the pregelatinized starch and a predetermined amount of microcrystalline cellulose, sodium carboxymethyl starch and hydroxypropyl methylcellulose, and placing the mixture into a dry-wet granulator to obtain a pre-mixed material;

3. Total mixing: adding the pre-mixed material into colloidal silicon dioxide, placing the mixture in a hopper mixer for mixing, and then adding magnesium stearate after mixing for total mixing; and 4. Tableting: tableting the totally-mixed intermediate with a 6-mm shallow concave punch and a hardness of 6 Kp-9 Kp.

Example 2: Powder Direct Compression

The pharmaceutical composition is prepared using a (powder) direct compression method. The ingredients and proportions used are given in the following table.

| Components | | mg/tablet | Percentage % (w/w) |
|---|---|---|---|
| Compound of formula I | Active ingredient | 0.5 | 0.59 |
| Microcrystalline cellulose | Diluent | 61.4 | 72.24 |
| Pregelatinized starch | Diluent | 18 | 21.18 |
| Sodium carboxymethyl starch | Disintegrant | 3.4 | 4.00 |
| Hydroxypropyl methylcellulose | Binder | 0.85 | 1.00 |
| Colloidal silicon dioxide | Lubricant | 0.425 | 0.50 |
| Magnesium stearate | Lubricant | 0.425 | 0.50 |
| Total amount | | 85 | 100 |

Preparation Method

1. Pretreatment: taking a predetermined amount of the compound of formula I, then taking pregelatinized starch with a weight ratio of the compound of formula I and the pregelatinized starch being 1:20 (the compound of formula I: pregelatinized starch, w/w=1:20), manually mixing the two, and sieving the mixture with a 60-mesh sieve to obtain a pre-treated material for later use;
2. Premixing: mixing the pre-treated material with the rest predetermined amount of the pregelatinized starch and a predetermined amount of microcrystalline cellulose, sodium carboxymethyl starch and hydroxypropyl methylcellulose, and placing the mixture into a dry-wet granulator to obtain a pre-mixed material;
3. Total mixing: adding the pre-mixed material into colloidal silicon dioxide, placing the mixture in a hopper mixer for mixing, and then adding magnesium stearate after mixing for total mixing; and
4. Tableting: tableting the totally-mixed intermediate with a 6-mm shallow concave punch and a hardness of 6 Kp-9 Kp.

Example 3: Powder Direct Compression

The pharmaceutical composition is prepared using a (powder) direct compression method. The ingredients and proportions used are given in the following table.

| Components | | mg/tablet | Percentage % (w/w) |
|---|---|---|---|
| Compound of formula I | Active ingredient | 2 | 2.35 |
| Microcrystalline cellulose | Diluent | 59.9 | 70.47 |
| Pregelatinized starch | Diluent | 18 | 21.18 |
| Sodium carboxymethyl starch | Disintegrant | 3.4 | 4.00 |
| Hydroxypropyl methylcellulose | Binder | 0.85 | 1.00 |
| Colloidal silicon dioxide | Lubricant | 0.425 | 0.50 |
| Magnesium stearate | Lubricant | 0.425 | 0.50 |
| Total amount | | 85 | 100 |

Preparation Method

1. Pretreatment: taking a predetermined amount of the compound of formula I and pregelatinized starch, manually mixing the two, and sieving the mixture with a 60-mesh sieve to obtain a pre-treated material for later use;
2. Premixing: mixing the pre-treated material with a predetermined amount of microcrystalline cellulose, sodium carboxymethyl starch and hydroxypropyl methylcellulose, and placing the mixture into a dry-wet granulator to obtain a pre-mixed material;
3. Total mixing: adding the pre-mixed material into colloidal silicon dioxide, placing the mixture in a hopper mixer for mixing, and then adding magnesium stearate after mixing for total mixing; and
4. Tableting: tableting the totally-mixed intermediate with a 6-mm shallow concave punch and a hardness of 6 Kp-9 Kp.

Example 4: Powder Direct Compression

The pharmaceutical composition is prepared using a (powder) direct compression method. The ingredients and proportions used are given in the following table. Referring to the method of Example 1, Example 4 was prepared:

| Components | | mg/tablet | Percentage % (w/w) |
|---|---|---|---|
| Compound of formula 1 | Active ingredient | 0.2 | 0.235 |
| Microcrystalline cellulose | Diluent | 61.7 | 72.59 |
| Pregelatinized starch | Diluent | 18 | 21.18 |
| Sodium carboxymethyl starch | Disintegrant | 3.4 | 4.00 |
| Hydroxypropyl methylcellulose | Binder | 0.85 | 1.00 |
| Colloidal silicon dioxide | Lubricant | 0.425 | 0.50 |
| Magnesium stearate | Lubricant | 0.425 | 0.50 |
| Total amount | | 85 | 100 |

Comparative Example 1: Dry Granulation

| Components | | mg/tablet | Percentage % (w/w) |
|---|---|---|---|
| Compound of formula I | Active ingredient | 0.05 | 0.06 |
| Microcrystalline cellulose | Diluent | 61.85 | 72.76 |
| Pregelatinized starch | Diluent | 18 | 21.18 |
| Sodium carboxymethyl starch | Disintegrant | 3.4 | 4.00 |
| Hydroxypropyl methylcellulose | Binder | 0.85 | 1.00 |
| Colloidal silicon dioxide | Lubricant | 0.425 | 0.50 |
| Magnesium stearate | Lubricant | 0.425 | 0.50 |
| Total amount | | 85 | 100 |

Preparation Method

1. Pretreatment: taking a predetermined amount of the compound of formula I, then taking pregelatinized starch with the weight ratio of the compound of formula I and the pregelatinized starch being 1:20 (the compound of formula I: pregelatinized starch, w/w=1:20), manually mixing the two, sieving the mixture with a 60-mesh sieve, and performing jet milling to obtain a co-powder for later use;
2. Premixing: mixing the co-powder with the rest predetermined amount of the pregelatinized starch and a predetermined amount of microcrystalline cellulose, sodium carboxymethyl starch (internally added part) and hydroxypropyl methylcellulose, sieving the mixture with a 60-mesh sieve, and mixing with a dry-wet granulator to obtain a pre-mixed material;
3. Dry granulation: performing dry granulation on the pre-mixed material;
4. Total mixing: adding the dry granulated material into sodium carboxymethyl starch (externally added part) and colloidal silicon dioxide, placing the mixture in a hopper mixer for mixing, and adding magnesium stearate after mixing for total mixing; and 5. Tableting: tableting the totally-mixed intermediate with a 6-mm shallow concave punch and a hardness of 6 Kp-9 Kp.

Comparative Example 2: Dry Granulation

| Components | | mg/tablet | Percentage % (w/w) |
|---|---|---|---|
| Compound of formula I | Active ingredient | 0.5 | 0.59 |
| Microcrystalline cellulose | Diluent | 61.4 | 72.24 |
| Pregelatinized starch | Diluent | 18 | 21.18 |
| Sodium carboxymethyl starch | Disintegrant | 3.4 | 4.00 |
| Hydroxypropyl methylcellulose | Binder | 0.85 | 1.00 |
| Colloidal silicon dioxide | Lubricant | 0.425 | 0.50 |
| Magnesium stearate | Lubricant | 0.425 | 0.50 |
| Total amount | | 85 | 100 |

Preparation Method

1. Premixing: taking a predetermined amount of the compound of formula I and pregelatinized starch, manually mixing the two, sieving the mixture with a 60-mesh sieve, then mixing the mixture with a predetermined amount of microcrystalline cellulose, sodium carboxymethyl starch (internally added part) and hydroxypropyl methylcellulose in a hopper mixer to obtain a premixed material;

2. Dry granulation: performing dry granulation on the pre-mixed material;

3. Total mixing: adding the dry granulated material into sodium carboxymethyl starch (externally added part) and colloidal silicon dioxide, placing the mixture in a hopper mixer for mixing, and adding magnesium stearate after mixing for total mixing; and 4. Tableting: tableting the totally-mixed intermediate with a 6-mm shallow concave punch and a hardness of 6 Kp-9 Kp.

Comparative Example 3: Dry Granulation

| Components | | mg/tablet | Percentage % (w/w) |
|---|---|---|---|
| Compound of formula I | Active ingredient | 2 | 2.35 |
| Microcrystalline cellulose | Diluent | 59.9 | 70.47 |
| Pregelatinized starch | Diluent | 18 | 21.18 |
| Sodium carboxymethyl starch | Disintegrant | 3.4 | 4.00 |
| Hydroxypropyl methylcellulose | Binder | 0.85 | 1.00 |
| Colloidal silicon dioxide | Lubricant | 0.425 | 0.50 |
| Magnesium stearate | Lubricant | 0.425 | 0.50 |
| Total amount | | 85 | 100 |

Preparation Method

1. Premixing: taking a predetermined amount of the compound of formula I and pregelatinized starch, manually mixing the two, sieving the mixture with a 60-mesh sieve, then mixing the mixture with a predetermined amount of microcrystalline cellulose, sodium carboxymethyl starch (internally added part) and hydroxypropyl methylcellulose in a hopper mixer to obtain a premixed material;

2. Dry granulation: performing dry granulation on the pre-mixed material;

3. Total mixing: adding the dry granulated material into sodium carboxymethyl starch (externally added part) and colloidal silicon dioxide, placing the mixture in a hopper mixer for mixing, and adding magnesium stearate after mixing for total mixing; and 4. Tableting: tableting the totally-mixed intermediate with a 6-mm shallow concave punch and a hardness of 6 Kp-9 Kp.

Experimental Example 1: Dissolution Experiment

A sample of Example 4 was subjected to a dissolution experiment using 900 mL of a phosphate buffer having a pH of 6.8 as a dissolution medium by using a dissolution testing method (according to the Method 2 of General Chapter 0931, *Chinese Pharmacopoeia*, Volume IV, 2015 Edition). The paddle method was used, the rotating speed was 50 rpm, and the dissolution was measured at 5, 10, 15, 20, 30, 45 and 60 minutes respectively. The results are shown in the table below:

| Time | Cumulative dissolution (%) Example 4 |
|---|---|
| 5 min | 73.5 |
| 10 min | 84.3 |
| 15 min | 87.3 |
| 20 min | 89.7 |
| 30 min | 94.6 |
| 45 min | 92.6 |
| 60 min | 95.4 |

As can be seen from the above results, the pharmaceutical composition disclosed herein has excellent dissolution properties. The dissolution after 20 min can reach 90% or higher.

Experimental Example 2: Stability Experiment

Samples of Comparative Example 1, Comparative Example 2, Comparative Example 3, Example 1, Example 2 and Example 3 were taken, and subjected to impurity measurement for day 0 and for 6 months under accelerated condition (40° C.±2° C., RH75%±5%). The measurement results are as follows:

| Examples | Time | Total impurities |
|---|---|---|
| Example 1 | Day 0 | 0.49% |
| | 6 months under accelerated condition | 0.63% |
| Example 2 | Day 0 | 0.44% |
| | 6 months under accelerated condition | 0.46% |
| Example 3 | Day 0 | 0.46% |
| | 6 months under accelerated condition | 0.48% |
| Comparative Example 1 | Day 0 | 1.34% |
| | 6 months under accelerated condition | 1.95% |

As can be seen from the above results, the pharmaceutical composition disclosed herein has high purity and excellent stability. In particular, the amount of total impurities remained almost unchanged under an accelerated testing condition for 6 months. In contrast, the comparative example showed a significant increase in the amount of total impurities up to 4-fold or more under an accelerated testing condition for 6 months. The impurity variation showed that the impurity increase of the pharmaceutical composition prepared by powder direct compression is significantly lower than that prepared by dry granulation. The pharmaceutical composition disclosed herein exhibits a significant stability advantage.

Experimental Example 3: Verification of Mixing Homogeneity

Samples of Example 2, Example 3 and Example 4 were taken, and subjected to mixing homogeneity measurement by using a content homogeneity testing method (according to General Chapter 0941, Chinese Pharmacopoeia, Volume IV, 2015 Edition), and the experiment comprises:
1. preparing a diluent, a mobile phase solution and a control solution according to the content homogeneity testing method;
2. randomly selecting 10 test tablets, accurately weighing each the test tablet, transferring the test tablets into volumetric flasks, respectively, adding a diluent, performing ultrasonic treatment for 10 min to disintegrate the tablets, cooling the reaction mixture to room temperature, diluting the reaction mixture with the diluent, and stirring the mixture with a stirrer for 2 h;
3. taking an appropriate amount of solution in a centrifuge tube, centrifuging at 8000 rpm for 10 min, pipetting a supernatant into an HPLC sample vial for sample injection, and measuring the content of the test samples; and
4. detection method: taking 10 samples, measuring a relative content $x_i$ of each sample in a single dose with a labeled amount of 100, respectively, and calculating an average value x, a standard deviation S $$S = \sqrt{\frac{\sum_{i=1}^{n}(x_i - \overline{X})^2}{n-1}}$$

and an absolute value A (A=|100−$\overline{X}$|) of the difference between the labeled amount and the average value. A lower A+2.2 S indicates a better homogeneity of the test samples. If A+2.2 S is less than or equal to 15.0, then the content homogeneity of the test samples meets the specification.
The measurement results are as follows:

| Examples | Specifications | Limit requirement | Results |
|---|---|---|---|
| Example 4 | 0.2 mg | 3.6 | |
| Example 2 | 0.5 mg | A + 2.2 S ≤ 15.0 | 6.6 |
| Example 3 | 2 mg | 2.4 | |

As can be seen from the above results, the pharmaceutical composition disclosed herein exhibits excellent mixing homogeneity and meets the limit requirement, and the actual testing results are much lower than the upper limit of the required testing results.

Experimental Example 4: Detection of Micromeritic Parameters and Particle Size Distribution Bulk density, tap density, Hausner ratio and particle size distribution were measured/calculated by taking the resulting mixtures, obtained after the completion of the total mixing step in the solid pharmaceutical composition of Comparative Example 2 and Example 2 in which the compound of formula I was 0.5 mg, respectively, as samples.

The bulk density was measured/calculated with a powder flowability tester BEP2. The tap density was measured/calculated with a packing density tester SOTAX TD1. The particle size distribution was measured/calculated with a vibration sieve instrument AS200 and using a mechanical sieving method. The results are as follows:

| Micromeritic properties | Comparative Example 2 | Example 2 |
|---|---|---|
| Bulk density g/mL | 0.556 | 0.446 |
| Tap density g/mL | 0.721 | 0.596 |
| Hausner ratio | 1.297 | 1.336 |

As can be seen from the above results, the pharmaceutical composition disclosed herein has specific micromeritic properties and exhibits good flowability.

| Particle size distribution % | Comparative Example 2 | Example 2 |
|---|---|---|
| <75 μm | 33.7 | 68.1 |
| 75 μm-150 μm | 19.7 | 30.4 |
| >150 μm | 46.6 | 1.6 |

As can be seen from the above results, a major amount of the particles in the pharmaceutical composition disclosed herein have a size of less than 75 μm, with a minor amount having a size of 75 μm-150 μm and only a small amount having a size of more than 150 μm.

Although typical embodiments have been illustrated and described herein, the present invention is not limited to the details. Since various possible modifications and substitutions do not deviate from the spirit of the present invention, those skilled in the art can use the variants and equivalents that can be conceived by routine tests, and therefore all these variants and equivalents fall within the spirit and protection scope defined by the appended claims.

The invention claimed is:
1. A solid pharmaceutical composition, comprising a compound of formula I, a diluent, a binder, a disintegrant, and a lubricant,

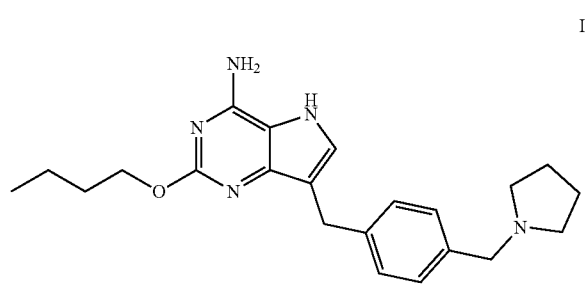 [SMILES: CCCCOc1nc(N)c2[nH]cc(Cc3ccc(CN4CCCC4)cc3)c2n1]

wherein:
the diluent is selected from the group consisting of microcrystalline cellulose, pregelatinized starch, and a mixture thereof;
the disintegrant is sodium carboxymethyl starch;
the binder is hydroxypropyl methylcellulose; and the lubricant is selected from the group consisting of magnesium stearate, colloidal silicon dioxide, and a mixture thereof;

wherein the solid pharmaceutical composition is prepared by a direct compression method.

2. The solid pharmaceutical composition according to claim 1, wherein, the solid pharmaceutical composition is a pharmaceutical composition in a unit dose form, and the mass of the compound of formula I in the composition per unit dose is 0.01 mg-10 mg; or the amount of the compound of formula I is selected from 0.01%-10% wt.

3. The solid pharmaceutical composition according to claim 1, wherein, the amount of the diluent is selected from 50% wt or more.

4. The solid pharmaceutical composition according to claim 3, wherein, the diluent comprises microcrystalline cellulose, and the amount of the microcrystalline cellulose is selected from 30%-90% wt; or the diluent comprises pregelatinized starch, and the amount of the pregelatinized starch is selected from 5%-35% wt; or the diluent is microcrystalline cellulose and pregelatinized starch.

5. The solid pharmaceutical composition according to claim 1, wherein, the amount of the disintegrant is selected from 1.0%-7.0% wt.

6. The solid pharmaceutical composition according to claim 1, wherein, the amount of the binder is selected from 0.1%-5% wt.

7. The solid pharmaceutical composition according to claim 1, wherein, the amount of the lubricant is selected from 0.1%-5% wt; or the lubricant comprises colloidal silicon dioxide, and the amount of the colloidal silicon dioxide is selected from 0.05%-3.0% wt; or the lubricant comprises magnesium stearate, and the amount of the magnesium stearate is selected from 0.05%-3.0% wt; or the lubricant is selected from the group consisting of colloidal silicon dioxide and magnesium stearate.

8. The solid pharmaceutical composition according to claim 1, wherein the solid pharmaceutical composition comprises:

0.02%-8.0% wt of the compound of formula I;

50% wt or more of microcrystalline cellulose, pregelatinized starch, or a mixture thereof;

1.0%-7.0% wt of sodium carboxymethyl starch;

0.1%-5% wt of hydroxypropyl methylcellulose; and 0.1%-5% wt of magnesium stearate, colloidal silicon dioxide, or a mixture thereof.

9. The solid pharmaceutical composition according to claim 1, wherein the solid pharmaceutical composition has at least one of the following characteristics:

the bulk density is less than or equal to 0.50 g/mL;

the tap density is less than or equal to 0.65 g/mL;

the Hausner ratio is 1.31-1.40; or particles, with an amount of more than or equal to 50%, have a size of less than 75 μm.

10. The solid pharmaceutical composition according to claim 1, wherein, the dosage form of the solid pharmaceutical composition may be selected from a powder, a granule, a tablet, a capsule, a pill, a pellet, a dispersion or an inhalable powder.

11. A method for preparing the solid pharmaceutical composition of the compound of formula I according to claim 1, comprising the direct compression method.

12. The method according to claim 11, comprising:

1) mixing the compound of formula I with part or all of the diluent and, optionally present, at least one of the binder, the disintegrant and the lubricant;

2) mixing the resulting mixture obtained in step 1) with the rest of the diluent and at least one of the rest of the binder, the disintegrant and the lubricant;

optionally, 3) mixing the resulting mixture obtained in step 2) with the rest of the excipients; and 4) tableting the resulting mixture obtained in step 2) or step 3).

13. The method according to claim 11, wherein, the method comprises the following steps: 1) preparing the compound of formula I, the diluent, the disintegrant, the binder and the lubricant into a mixture; and 2) tableting.

14. The method according to claim 11, wherein, the mixture comprising the compound of formula I and the diluent is not subjected to milling.

15. A method for treating a disease associated with TLR7, comprising administering to a subject in need thereof the solid pharmaceutical composition of the compound of formula I according to claim 1.

* * * * *